US011160568B1

(12) United States Patent
Park

(10) Patent No.: US 11,160,568 B1
(45) Date of Patent: Nov. 2, 2021

(54) OPTIMAL SELECTION OF CONTACT CURVES

(71) Applicant: Lento Medical Inc., Houston, TX (US)

(72) Inventor: Ilwhan Park, Walnut Creek, CA (US)

(73) Assignee: Lento Medical, Inc, Houston, TX (US)

( * ) Notice: Subject to any disclaimer, the term of this patent is extended or adjusted under 35 U.S.C. 154(b) by 150 days.

(21) Appl. No.: 16/565,836

(22) Filed: Sep. 10, 2019

(51) Int. Cl.
| | | |
|---|---|---|
| A61B 17/58 | (2006.01) |
| A61B 17/60 | (2006.01) |
| A61F 2/00 | (2006.01) |
| A61B 17/17 | (2006.01) |
| A61B 17/56 | (2006.01) |
| A61B 17/15 | (2006.01) |

(52) U.S. Cl.
CPC ........ *A61B 17/1764* (2013.01); *A61B 17/155* (2013.01); *A61B 17/56* (2013.01)

(58) Field of Classification Search
CPC combination set(s) only.
See application file for complete search history.

(56) References Cited

U.S. PATENT DOCUMENTS

| | | | |
|---|---|---|---|
| 5,347,215 | A | 9/1994 | Armstrong et al. |
| 5,417,694 | A | 5/1995 | Marik et al. |
| 7,998,203 | B2 | 8/2011 | Blum |
| 8,066,708 | B2 | 11/2011 | Lang et al. |
| 8,323,288 | B2 | 12/2012 | Zajac |
| 8,403,994 | B2 | 3/2013 | Maloney et al. |
| 8,617,175 | B2 | 12/2013 | Park et al. |
| 8,623,026 | B2 | 1/2014 | Wong et al. |
| 8,777,875 | B2 | 7/2014 | Park |
| 9,023,111 | B2 | 5/2015 | Walker |
| 9,579,107 | B2 | 2/2017 | Schoenefeld |
| 9,730,810 | B2 | 8/2017 | Fisher et al. |
| 9,744,044 | B2 | 8/2017 | Cohen et al. |
| 9,826,981 | B2 | 11/2017 | Schoenefeld et al. |
| 9,883,871 | B2 | 2/2018 | Park |
| 10,206,695 | B2 | 2/2019 | Meridew et al. |
| 10,206,697 | B2 | 2/2019 | Metzger et al. |
| 10,226,262 | B2 | 3/2019 | Kehres et al. |

(Continued)

FOREIGN PATENT DOCUMENTS

WO WO2001070143 A1 9/2001

*Primary Examiner* — Sameh R Boles
(74) *Attorney, Agent, or Firm* — Mark Prostik; Thomas Schneck

(57) ABSTRACT

A cutting jig and corresponding method of manufacture is provided. The jig comprises a unitary piece combining a bone cutting guide defining a cut plane and a set of fins projecting from a jig substrate and terminating in curvilinear bone-jig contact surfaces for abutting articular surface features. The curvilinear surfaces are characterized by custom patient-specific parameters derived from measurements obtained from selected image slices of a patient's joint region such that the curvilinear surfaces establish one and only one mechanical self-locking position for the unitary piece. One obtains a series of image slices of a patient's joint region, then selects a set of slices that show specified articular surface features in the joint region. Patient-specific parameters obtained from measurements of the slices specify curvilinear bone-jig contact surfaces and a cut plane. The contact surfaces at the ends of the fins may be extruded as stepped set of line segments that follow curves along the articular surface features.

4 Claims, 9 Drawing Sheets

(56) References Cited

U.S. PATENT DOCUMENTS

| | | |
|---|---|---|
| 10,271,861 B2 | 4/2019 | Riva |
| 2009/0319049 A1 | 12/2009 | Shohet |
| 2013/0296860 A1 | 11/2013 | Chana et al. |
| 2015/0088142 A1 | 3/2015 | Gibson |
| 2015/0105698 A1* | 4/2015 | Park ................ A61B 17/155 600/587 |
| 2019/0239903 A1* | 8/2019 | Park ................ A61B 17/155 |

* cited by examiner

OPTIMAL SELECTION OF CONTACT CURVES

TECHNICAL FIELD

This invention relates to orthopedic knee replacement. More particularly, the invention relates to surgical jigs for guiding bone resectioning in knee replacement surgery, and to the manufacture of such jigs, such that each jig is patient-specific with custom specifications determined from MRI slices of a patient's tibio-femoral joint region.

BACKGROUND ART

Femoral and tibial surgical cutting jigs are used to guide bone resectioning in knee replacement surgery. Each jig contains both the various bone-jig contact surfaces and a cutting guide defining a cut plane. In order that the cut planes are correct when the respective jigs are installed during surgery, each jig must be custom manufactured to correspond to a patient's own femur and tibia. Magnetic resonance imaging (MRI) of a patient's tibio-femoral joint region is performed prior to surgery to define the parameters needed to manufacture patient-specific jigs.

Some arthroplasty jigs employ only planar contact surfaces (much like a vise) that do not offer a unique jig position and thus requires greater skill on the part of the surgeon to get the alignment right. Still other jigs are of the sparse contact type with multi-point contacts in the form of tips or pins. This type of jig also tends to allow more than one possible positioning of the jig against the joint, rather than only one fit.

Thus, one problem in parameterizing the surface features from the MRI scans and creating the jig, is that prior methods of point-to-point type bone-jig contact do not provide unique mechanical self-locking with respect to features in the tibio-femoral joint region. The jig has sufficient play over the end of the bone as to yield unacceptable levels of uncertainty in the cut plane. Instead, the jig should have one and only one mechanical self-locking position such that the bone cutting guide defines a single unique cut plane to guide the surgeon during bone resectioning.

In U.S. Pat. No. 8,323,268, Zajac describes patient-specific femoral and tibial cutting blocks that have bone-facing surfaces with customized negative contours. When the cutting blocks are used, the bone-facing surfaces receive a corresponding positive contour of a portion of a patient's femur or tibia to contact with a unique position or location on the bone. In particular, bone-facing surfaces may contact specified portions of anterior, distal and posterior sides of a femur and likewise with medial and proximal sides of a tibia.

In U.S. Pat. No. 8,617,175, Park describes femoral and tibial arthroplasty jigs with a mating surface on one side. The mating surfaces include a customized surface contour that is generally a negative of corresponding femoral and tibial target surfaces.

In U.S. Pat. No. 10,206,697, Metzger et al. describe a femoral alignment guide with a patient-specific 3D curved inner surface the mates with a corresponding femoral joint surface of the patient.

SUMMARY DISCLOSURE

This invention provides patient-specific cutting jigs, whose mating mechanism consists of a set of multiple projecting fins that terminate in curvilinear contacts that mate with respective distal femur and proximal tibia joint surfaces to ensure accurate bone resections. FIG. 1 illustrates the articular surface of the distal end of a femur, consisting of trochlear groove (TG) and lateral/medial condyles (LC/MC) with respect to a femoral axis 11. FIG. 2 illustrates the articular surface of the proximal end of a tibia, consisting of lateral/medial plateaus (LTP/RTP), tibial spine (TS) and anterior intercondylar Area (AIA) with respect to a tibial axis 21. FIGS. 3 and 4 show femoral and tibial arthroplasty jigs FCJM and TCJM that each have three curvilinear curves CA1, CA2 and CA3, which mate onto the articular surfaces of respective distal femur and proximal tibia.

The cutting jigs FCJM and TCJM illustrated in FIGS. 3 and 4 have a first number N1 of isolated contact locations that make contact with a similar number of corresponding isolated contact locations on the trochlear groove (TG) surface of the femur, or on the mid-tibial plateau surface of the tibia, and that also make contact with a second number N2 of isolated contact locations on the lateral/medial condyles (MC/LC) of distal femur, or on the anterior intercondylar area (AIA) surface of proximal tibia, where the sum, N1+N2, is no greater than 12, and can be made as small as 2 in some approaches. The number, N1+N2, of isolated contact locations (non-collinear) and their placement and orientation on the femur or tibia surfaces is chosen so that each contact point of the curvilinear curve on the cut plane mechanism makes contact with a corresponding contact point of the curvilinear curves on the cutting jig mechanism FCJM or TCJM.

For example, the cutting jig mechanism FCJM is positioned in contact with the lateral/medial condyles (LC/MC) and the trochlear groove TG on the femur, and two or more FCJM positioning apertures (drill holes) are drilled through the FCJM and into a portion of cortical bone of the patient. This provides a cut plane guide for resection and removal of a lower portion of the patient's femur. After resection has occurred, the cut plane bar is removed and optionally might be reused in replacement of another patient's knee. A similar procedure is followed for replacement of a tibia using the tibial cutting jig mechanism TCJM. In the following, contact curvilinear curves are estimated for both femur and tibia components.

Accordingly, a cutting jig of the present invention comprises a unitary piece combining a bone cutting guide defining a cut plane and a set of curvilinear bone-jig contact surfaces (defined by curves CA1, CA2 and CA3 in FIGS. 3 and 4) projecting from a jig substrate for abutting articular surface features. The curvilinear surfaces are further characterized by custom patient-specific parameters derived from measurements obtained from selected image slices of a patient's joint region such that the curvilinear surfaces establish one and only one mechanical self-locking position for the unitary piece.

More particularly, the custom patient-specific parameters are obtained from a sequence of image slices, defining x-y image planes and a separation distance $\Delta z$ between image slices. First, one forms at least one sequence of curves from projections of the image slices for one or more selected viewing angles $\varphi$ relative to the respective x-y image planes. The curves follow medial and lateral condyles of ends of respective femur and tibia proximate to a region of the knee as identified in the image slices. Each curve is approximated as a polynomial in its x-y image plane, which is then projected by geometric transformation onto rotated planes that correspond to the selected viewing angles $\varphi$. Finally, the viewing angles $\varphi$ are constrained to meet a non-intersection condition on the respective sequences of curves, leading to a selection of curves for jig formation. The curvilinear contact surfaces may be manufactured in accord with those curves projected onto rotated planes for the constrained viewing angles by extruding step structures in the form of fins in the direction of the rotated planes and that terminate in a stepped set of line segments that follow the projected curves.

DETAILED DESCRIPTION

This invention provides a method, and corresponding apparatus, for determining a small number (≥2) of contact curves located on a femur and tibia, for locating and orienting a cut plane appliance, commonly referred to as a surgical cutting jig, that can be used in a total knee replacement.

Figure 3:
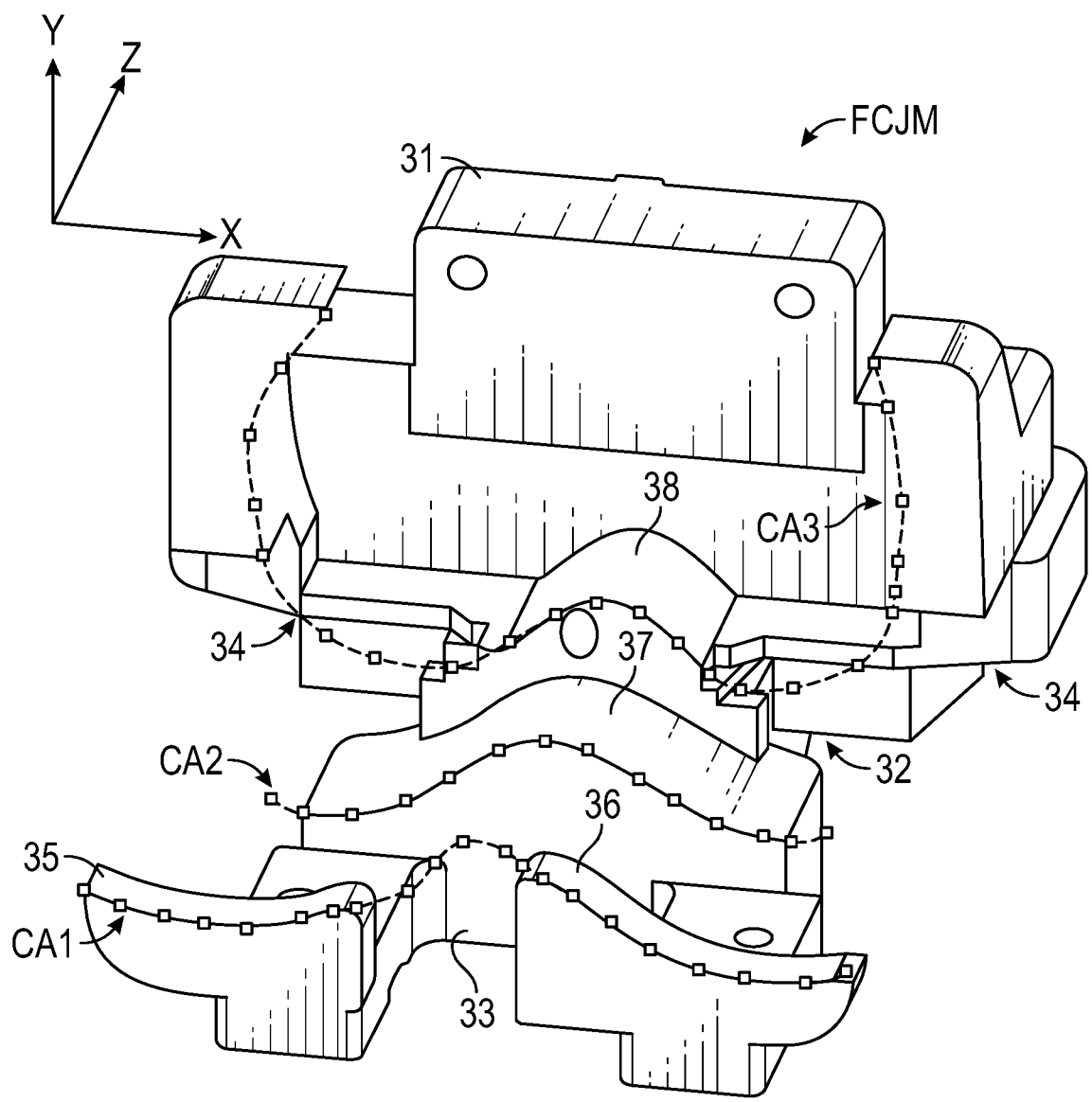
FIG. 3 is an isometric view of a femoral cutting jig mechanism FCJM.

With reference to FIG. 3, a femoral cutting jig FCJM is seen to have a front plate 31 coupled to an end plate 33 at an elbow joint 32. The front plate 31 has at least one planar slot 34 therein coinciding with a desired cut plane when the jig is installed onto a femur. The front plate 31 has a pair of anterior feet 35 and 36 with curvilinear surfaces (left and right portions of CA3) thereon for contact with anterior sides of respective medial and lateral condyles MC and LC of a patient's femur. The end plate 33 has a pair of posterior feet with curvilinear surfaces CA1 and CA2 thereon for contact with condylar surfaces of the respective medial and lateral condyles MC and LC. The end plate 33 also has at least one posterior projection 37 and 38 proximate to the elbow joint 32 and having a convex curvilinear surface (center portion of CA3) for contact with trochlear groove TG surfaces in an intercondylar region of the femur.

Figure 4:
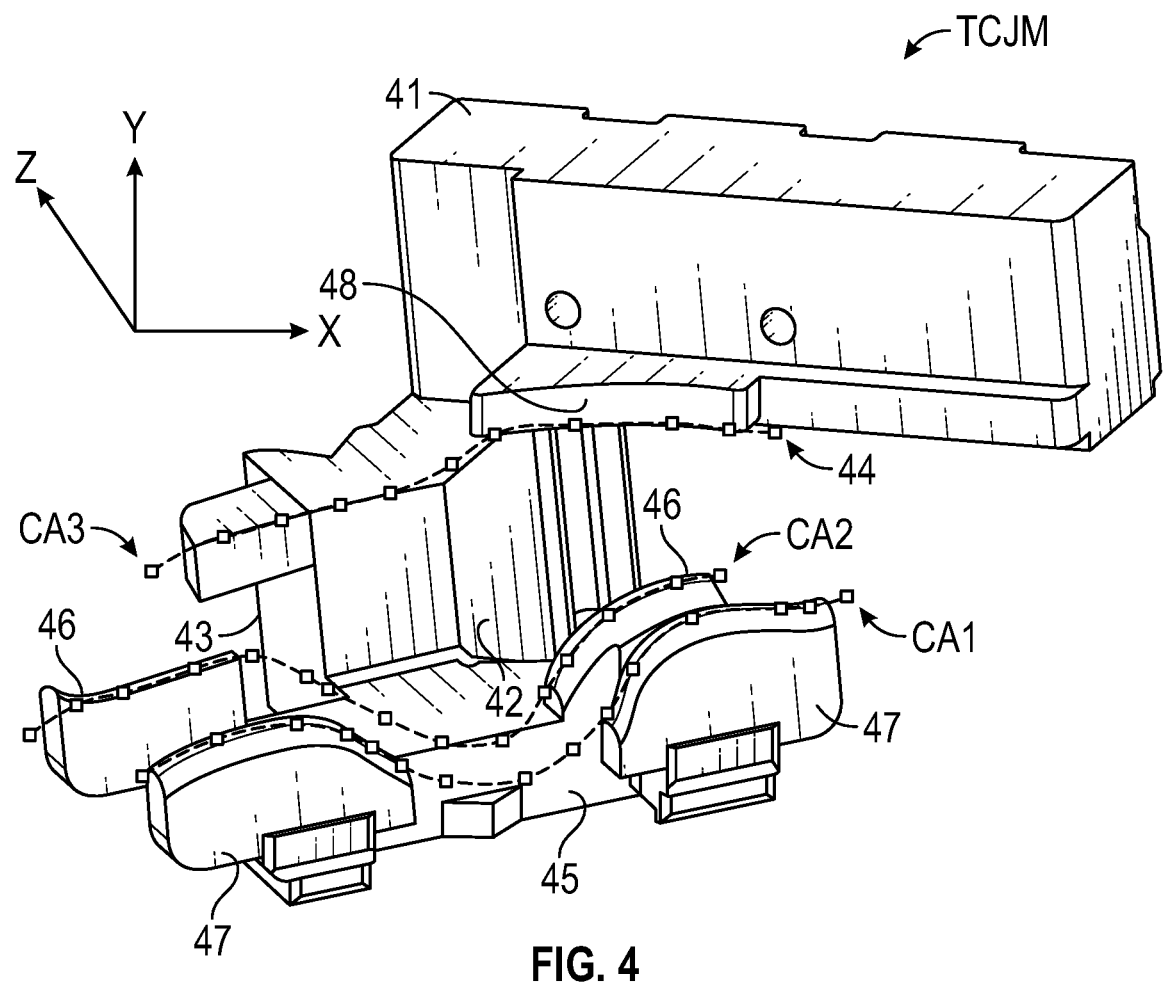
FIG. 4 is an isometric view of a tibial cutting jig mechanism TCJM.

With reference to FIG. 4, a tibial cutting jig TCJM has a main medial block 41 and a front plate 43 coupled to the main medial block 41 at an elbow joint 42. The main plate 41 has at least one planar slot 44 therein coinciding with a desired cut plane when the jig is installed onto a tibia. An end extension 45 projects from a superior posterior surface of the front plate 43 and has pairs of medial and lateral posterior feet 46 and 47 with downward projections. The main medial block 41 has a concave extension 48 on an interior side of the elbow joint 42 and terminating in curvilinear contact CA3 that abuts a side surface of the tibia. The downward projections of the posterior feet 46 and 47 have underside curvilinear surfaces CA1 and CA2 for contact with the lateral and medial tibial plateaus LTP and MTP at a position anterior to the tibial spine TS.

The number of femur or tibia contact curves can be as small as 2-5, or can be larger if desired, depending upon the femur topography and the degree of stability desired. A Cartesian coordinate system (x, y, z) is established, with fixed z-axis oriented parallel to a unit length vector $\bar{u}$, which is perpendicular to a sequence of spaced apart xy-planes that are coincident with a sequence of planes defined by MRI planes. The MRI planes are spaced apart by a non-zero separation distance $\Delta z = z_{n+1} - z_n$, either constant or variably as illustrated in FIG. 5.

Figure 1:
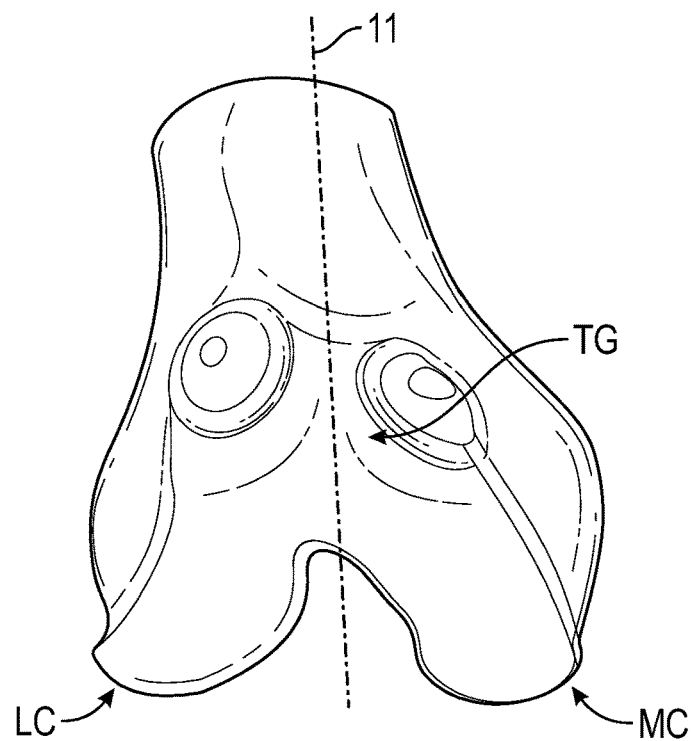
FIG. 1 illustrates an assembly of medial/lateral condyles and a trochlear groove as components of femur.
Figure 2:
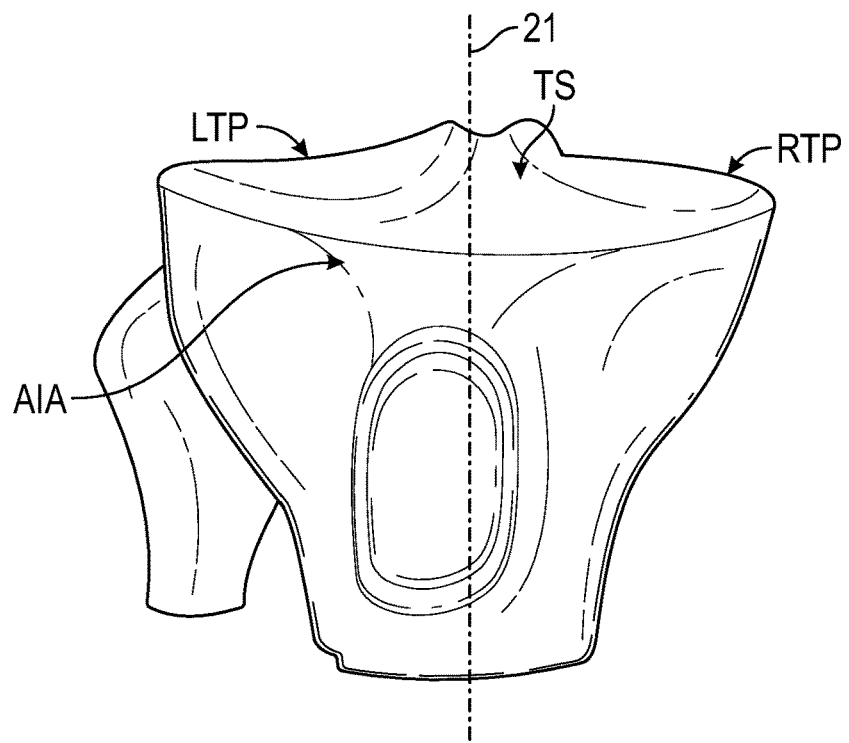
FIG. 2 illustrates an assembly of medial/lateral tibial plateau and a tibial spine as components of tibia.
Figure 5:
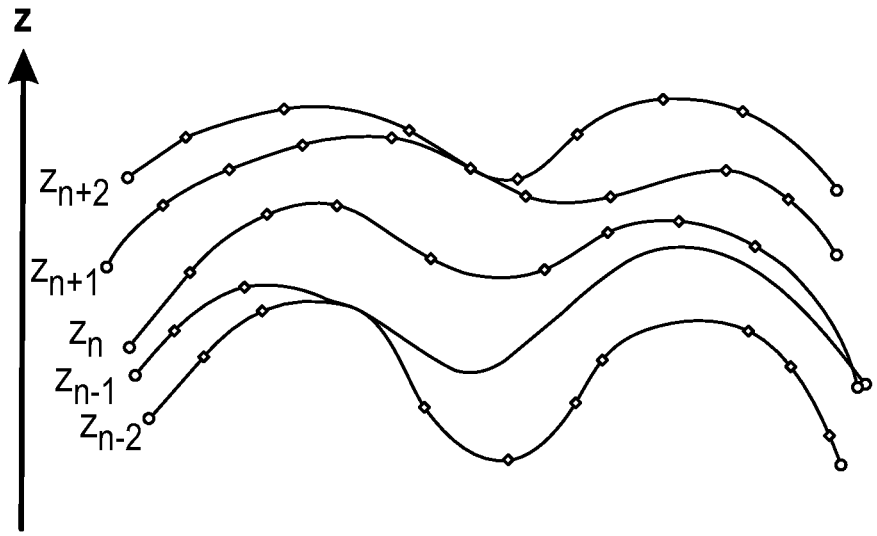
FIG. 5 illustrates an embodiment of a sequence of curves resulting from projections of MRI images ("slices of a portion of either femur of tibia onto MRI images planes, $z=z_{n-2}, z=z_{n-1}, z=z_n, z=z_{n+1}, z=z_{n+2}$, viewed from a selected viewing angle φ relative to an xy-plane.

A medial condyle MC and the corresponding lateral condyle LC of the distal femur (FIG. 1) projected onto a sequence of xy-planes ( . . . , $z_{n-2}, z_{n-1}, z_n, z_{n+1}, z_{n+2}$ . . . ) are represented by curves obtained from a sequence of the MRI image planes, as illustrated in FIG. 5. In one embodiment, a sequence of MRI images provides an approximation for the local surface topography of the medial condyle and of the adjacent lateral condyle of the knee; and each of the sequence of MRI images represents a projection of the two condyles and trochlear groove onto an MRI image plane, which defines a sequence of "slices" in FIG. 5.

Each of a sequence $\{P(z_n)\}_n$ of z-axis projections (MRI images) onto one of the xy-planes (e.g., $z=z_n$) is a curve that can be approximated (see FIG. 6) as a polynomial, $y=Q_n(x)$, lying in the xy-plane and comprising three consecutive y-extremum values: a first y-maximum (e.g., lateral condyle), an intermediate y-minimum (e.g., trochlear groove), and a second y-maximum (e.g., medial condyle) at x-values and corresponding y-values $$(x,y)=(x_{n,1},y_{n1}),(x_{n,2},y_{n2}),(x_{n,3},y_{n3})(n=1,2,\ldots,N;N\geq 2) \quad (1)$$

Figure 6:
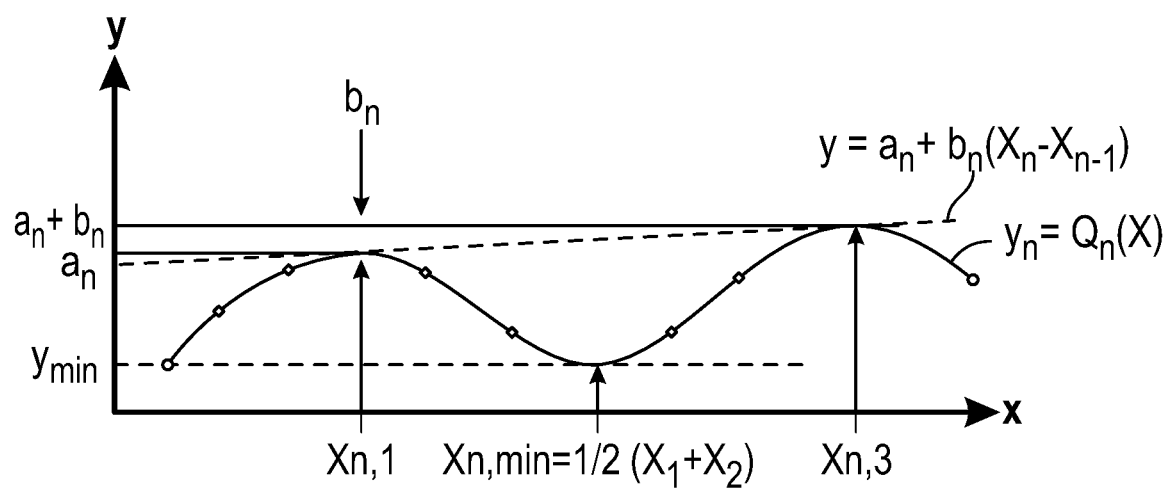
FIG. 6 illustrates one of a first sequence of curves, $y(s)=Q_n(x)$, that approximates one of the femur or tibial curve projections shown in FIG. 5.

As illustrated in FIG. 6, only a selected interval of x-values and corresponding extremum y-value amplitudes are shown. Each of the sequence of curves illustrated in FIG. 5 can be approximated by a polynomial in x:

$$y = Q_n(x) = a_n + b_n(x - x_{n,1}) - u_{n0}\{(x - x_{n,1})^2(x - x_{n,3})^2\}, \quad (2\text{-}A)$$

$$(dy/dx)_{x_{n,1}} = (dy/dx)_{x_{n,2}} = (dy/dx)_{x_{n,3}} = 0, \quad (2\text{-}B)$$

$$Q_n(x_{n,1}) = a_n = y(x_{n,1}), \quad (3)$$

$$Q_n(x_{n,2}) = a_n + b_n(x_{n,2} - x_{n,1}) = y(x_{n,3}), \quad (4)$$

$$b_n = (y(x_{n,3}) - y(x_{n,1}))/(x_{n,3} - x_{n,1}), \quad (5)$$

where the line segment $y(x) = a_n + b_n(x - x_{n,1})$ passes through the points, $(x_{n,1}, y_{n,1})$ and $(x_{n,3}, y_{n,3})$. Alternatively, the three consecutive y-extremum values may be a first y-minimum, an intermediate y-maximum, and a second y-minimum, and the polynomial approximation in Eq. (2-A) is replaced by an alternative expression, $$y = Q_{n,alt}(x) = a_n + b_n(x - x_{n,1}) + u_{n0}\{(x - x_{n,1})^2(x - x_{n,3})^2\}, \quad (2\text{-}C)$$

$$a_n + b_n x_{n,3} = Q(x_{n,3}), \quad (2\text{-}D)$$

and Eqs. (3)-(5) are unchanged.

Returning to Eqs. (2-A) and (2-B), a minimum value for $Q_n(x)$ ($x_{n,1} < x < x_{n,3}$) is determined from $$\{(\partial Q_n(x))/\partial x\} = b_n - 4u_{n0}\{(x - x_{n,1})^2(x - x_{n,3})^2\} \approx 0, \quad (6)$$

$$x_{n,13} = (x_{n,1} + x_{n,3})/2, \quad (7)$$

Eq. (6) is a cubic equation in the unknown, $x_{n,min}$, with at least one determinable real root, $x = x_{n,min}$. A suitable approximation for $x_{n,min}$ is $$x_{n,min} = x_{n,13} + c_n b_n, \quad (8)$$

$$c_n = -1/\{4u_{n,0}(x_{n,1} - x_{n,3})^2\}, \quad (9)$$

$$Q_n(x_{min}) = a_n + b_n x_{n,min} - u_{n,0}(x_{n,min} - x_{n,1})^2(x_{n,min} - x_{n,3}) = Q_{n,min}, \quad (10)$$

where $x = x_{n,min}$ is a real solution of the cubic equation in Eq. (6), and $Q_{n,min}$ is a measured (minimum) value that determines the value of the parameter $u_{n,0}$.

Figure 7:
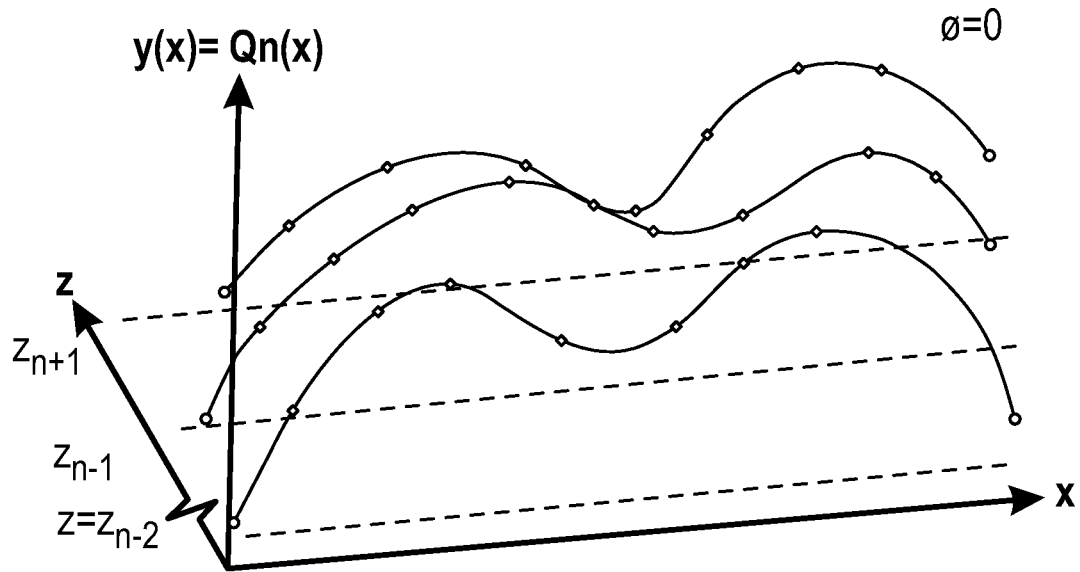
FIG. 7 illustrates an embodiment of a second sequence of curves that approximate a sequence of femur or tibia curve projections from a viewing angle φ=0.

A difference of two (not necessarily consecutive) approximation polynomials, $$\Delta Q_{n2}(x) = Q_{n1}(x) Q_{n2,n1}(x), \quad (11)$$

is computed for each of a sequence of selected x-coordinate values, $x = x_p$ (independent of fixed indices n1 and n2) in a selected x-interval, $x_{LB} \leq x_{UB}$. Ideally, the values $\Delta Q_{n2,n1}(x)$ satisfy $$\Delta Q_{n2,n1}(x_p) > 0 (1 \leq n1 < n2 \leq N), \quad (12)$$

for each of the selected values, $x = x_p$ ($p = 1, \ldots, P \geq 2$), so that the two approximation polynomials, $Q_{n1}(x_p)$ and $Q_{n2}(x_p)$, do not intersect with each other. This condition of non-intersection is unlikely to occur for some value pairs (n1, n2) of the indices. Values, $\Delta Q_{n2,n1} > 0$, $\Delta Q_{n2,n1}(x_p) = 0$ or $\Delta Q_{n2,n1}(x_p) < 0$, with n fixed, as illustrated in FIG. 7 for $\Delta Q_{n1}(x)$ and $\Delta Q_{n1+1}(x)$, with viewing angle $\varphi = 0$.

Figure 8:
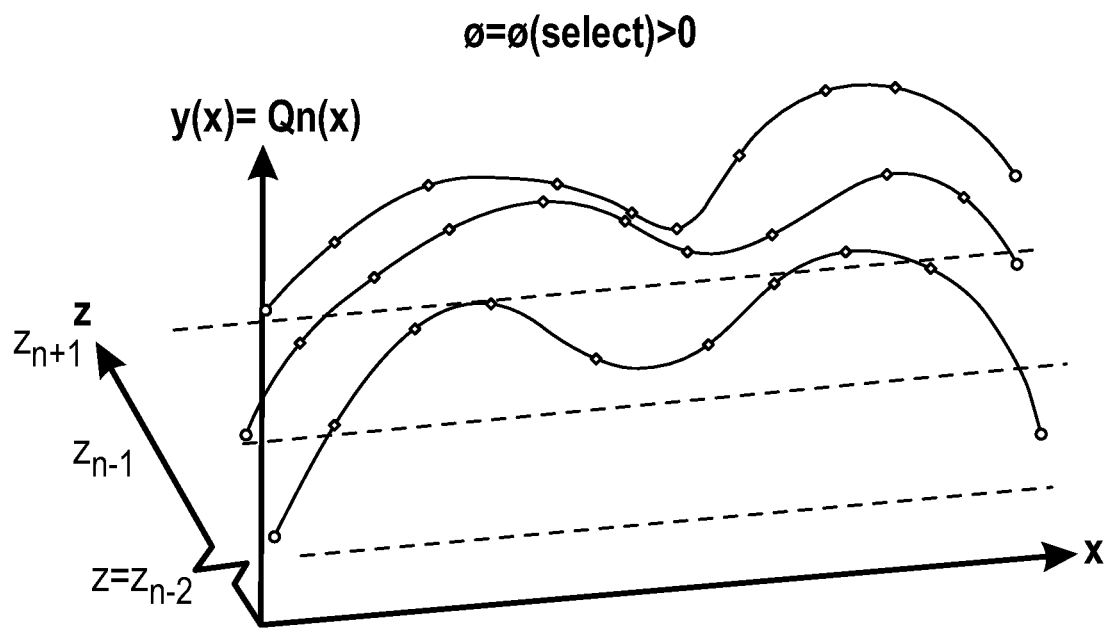
FIG. 8 illustrates an embodiment of a second sequence of curves that approximate a sequence of femur or tibia curve projections from a viewing angle φ>0 relative to an xy-plane.

However, if the sequence of approximation polynomials $\Delta Q_{n1,n2}(x_p)$ is viewed at a selected non-zero viewing angle $\varphi$ ($0 < \varphi < \pi$), as illustrated in FIG. 8, the non-intersection condition set forth in Eq. (12) may be satisfied. FIG. 8 views the femur surface in a direction of a vector lying in or parallel to a slice surface and satisfies the non-intersection condition in Eq. (12) for all index pairs (n1, n2) (n1 < n2). For a particular (consecutive or non-consecutive) pair of MRI slices, a first viewing angle $9 < \pi/2$ may also suffice, and/or a second viewing angle $\varphi > \pi/2$ may also suffice. For fixed indices n1 and n2, the polynomial values, $\Delta Q_{n2,n1}(x_p) > 0$, $\Delta Q_{n2,n1}(x_p) = 0$ and $\Delta Q_{n2,n1}(x_p) < 0$, are preferably treated separately, because the permitted ranges of the viewing angle $\varphi$ are separately defined for each condition.

Viewing of a polynomial difference $\Delta Q_{n2,n1}(x)$ for two consecutive MRI slices at an angle $\varphi$ is implemented by a geometric transformation from the original coordinate system (x, y, z) to a rotated coordinate system (x', y', z'), $$\begin{bmatrix} x' \\ y' \\ z' \end{bmatrix} = \begin{bmatrix} 1 & 0 & 0 \\ 0 & \cos\phi & \sin\phi \\ 0 & \sin\phi & \cos\phi \end{bmatrix} \begin{bmatrix} x \\ y \\ z \end{bmatrix} = \begin{bmatrix} x \\ y\cos\phi + z\sin\phi \\ -y\sin\phi + z\cos\phi \end{bmatrix}, \quad (13)$$

Note that under this transformation the value of each of the selected x-coordinate values, $x'_p = x_p$, are unchanged. Under this transformation, the quantities of interest, $(\Delta Q_{n2,n1}(x), \Delta_{zn2,n1}) = (Q_{n2}(x) - Q_{n1}(x), z_{n2} - z_{n1})$ become transformed to $$\{Q_{n+1}(x) - Q_n(x)\}' = \{Q_{n2}(x) - Q_{n1}(x)\} \cdot \cos\varphi + \{z_{n2} - z_{n1}\} \cdot \sin\varphi = \Delta Q_{n2n1}(x,\varphi), \quad (14)$$

$$\{z_{n21} - z_{n1}\}' = -\{(Q_{n+1}(x) - Q_{n1}(x)\} \cdot \sin\varphi + \{z_{n+1} - z_n\} \cdot \cos\varphi = \Delta z_{n+1}(\varphi), \quad (15)$$

$$z_{n2} - z_{n1} = (n2 - n1) \cdot \Delta z, \quad (16)$$

where $\Delta z$ is a known and fixed distance between two consecutive slices. The non-intersection condition in Eq. (12) becomes $$\Delta Q_{n2,n1}(x,\varphi) = \Delta Q_{n2,n1}(x_p) \cdot \cos\varphi + \Delta z_{n+1} \cdot \sin\varphi = \{(Q_{n2,n1}(x_p))^2 + (\Delta z_{n2,n1})^2\}^{1/2} \cdot \{\sin\{(\varphi + \tan^{-1}[(\Delta Q_{n2,n1}(x_p)/\Delta z_{n2,n1})]\} > 0. \quad (17)$$

Equations (14) and (15) apply to any pair of slices, $z = z_{n1}$ and $z = z_{n2}$ ($1 \leq n1 < n2 \leq N$). An arithmetic average value of the values $\Delta Q_{n2,n1}(x_p)/\{(n2 - n1)\Delta z\}$.

For a fixed slice pair (n2, n1), Eq. (12) should be satisfied for each selected x-value, $x = x_p$ in the selected sequence $\{x_p\}$. Each selected coordinate value, $x = x_p$, may require a different range of the viewing angles $\varphi$ so that $\varphi$ becomes dependent upon the index n and upon the coordinate value, $x = x_p$: $\varphi = \varphi(n2; n1; x_p)$. The coordinate difference, $\Delta z_{n2n1}$ is always positive and constant so that the signum of the ratio $$R = R(n2; n1; x_p) = \Delta Q_{n2,n1}(x_p)/(N\Delta z), \quad (18\text{-}1)$$

is the signum of the numerator $\Delta Q_{n2,n1}(x_p)$. For definiteness, where $\Delta Q_{n2,n1}(x_p) < 0$, write $$R = -|R(n2; n1; x_p)| = -|(\Delta Q_{n2,n1}(x_p))/N\Delta z|(R < 0), \quad (18\text{-}2)$$

$$R = |R(n2; n1; x_p)| = |(\Delta Q_{n2,n1}(x_p))/N\Delta z|(R > 0). \quad (18\text{-}3)$$

From a consideration of the different circumstances, one verifies that the angle $\varphi$ that satisfies the non-intersection condition in Eq. (12) is constrained as follows:

$$\Delta Q_{n+1}(x_p) > 0: -\tan^{-1}(R) < \varphi < \pi - \tan^{-1}(R)(R > 0), \quad (19\text{-}1)$$

$$\Delta Q_{n+1}(x_p) > 0: 0 < \varphi < \pi(R = 0), \quad (19\text{-}2)$$

$$\Delta Q_{n+1}(x_p) > 0: -\{\pi + \tan^{-1}(|R|)\} < \varphi < \tan^{-1}(|R|)(R < 0) \quad (19\text{-}3)$$

Figure 9:
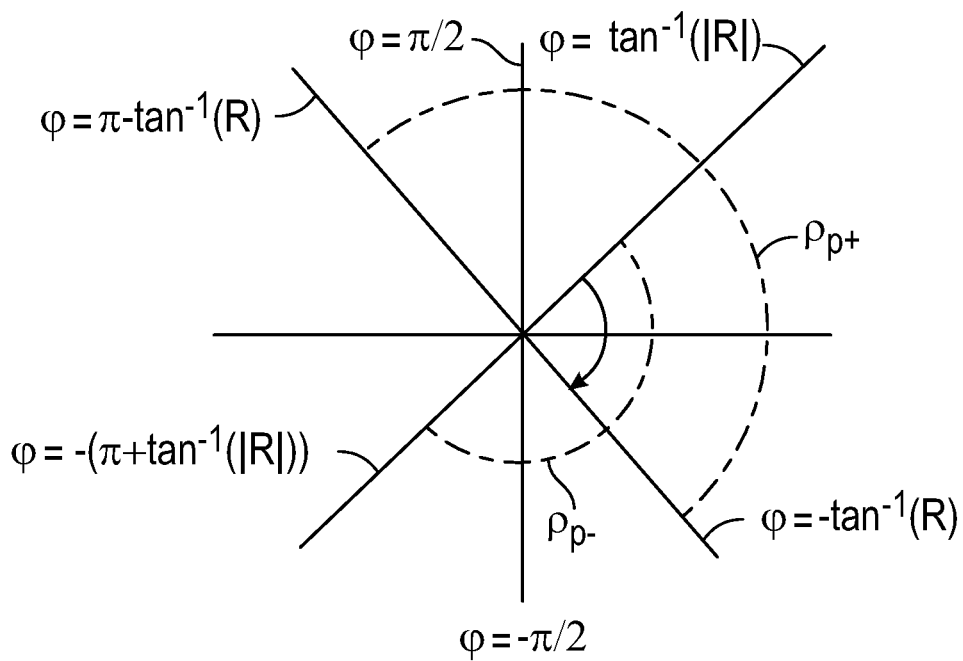
FIG. 9 graphically illustrates constraint ranges for a femur or tibia viewing angle β corresponding to a non-intersection condition.

The $\varphi$-ranges for each of the three $\varphi$-constraints in Eqs. (19-1)-(19-3) overlap and are illustrated graphically in FIG. 9. These $\varphi$-constraints correspond to the following respective $\varphi$-ranges:

$$\rho_{p+} = \{\varphi | -\tan^{-1}(R) < \varphi < \pi - \tan^{-1}(R)\}(R > 0) \quad (20\text{-}1)$$

$$\rho_{p0} = \{\varphi | 0 < \varphi < \pi\}(R = 0) \quad (20\text{-}2)$$

$$\rho_{p-} = \{\varphi | -\{\pi + \tan^{-1}(R)\} < \varphi < \tan^{-1}(R)\}(R < 0) \quad (20\text{-}3)$$

And each of these three φ-ranges sets is summed over all x-coordinate values, $x=x_p$, that satisfy the corresponding φ-constraint set forth in the φ-constraint sets, Eq. (20-1), (20-2) and (20-3). The dotted curvilinear segments in FIG. 9, identified as $\rho_{p+}$ and $\rho_{p-}$ indicate the φ-range corresponding to $\rho_{p+}$ and $\rho_{p-}$ set forth in Eqs. (20-1) and (20-3), respectively. Where no x-coordinate, $x=x_{p0}$, satisfies $\Delta Q_{n2,n1}(x_{p0})=0$ ($x_{p0}$ is an empty set), the φ-constraint in Eq. (20-2) is not imposed.

Each of the sets, $\rho_{p+}$, $\rho_{p0}$ and $\rho_{p-}$, of φ-values corresponds to a mutually exclusive set of x-coordinate values, $x=x_p$, and to a fixed choice of index n; and one or more of the corresponding x-coordinate sets may be empty. For a fixed slice index value n, a three-way intersection of permitted ranges of the angle φ, $$\rho_p(n)=\rho_{p+}\cap\rho_{p0}\cap\rho_{p-} (\rho_{p0}\text{ non-empty}) \quad (21\text{-}1)$$

$$\text{or } \rho_p(n)=\rho_{p+}\cap\rho_{p-} (\rho_{p0}\text{ empty}) \quad (21\text{-}2)$$

of the three φ-constraint sets defines the permissible range for the viewing angle φ that satisfies the non-intersection condition Eq. (12) for fixed slice indices, n2 and n1. Note that the intersection condition $\rho_p(n)$ must be determined separately for each pair of consecutive MRI slices ($z=z_{n2}$ and $z=z_{n1}$) of interest. The set intersection $\rho_p(n)$ can also be characterized as $$\rho_p(n)=\{\theta\max\{\tan^{-1}(R)\}<\varphi<\pi-\max\{\tan^{-1}(R)\}\}, \quad (22)$$

where the first $\max\{\tan^{-1}(R)\}$ term in Eq. (20-1) and the second $\max\{\tan^{-1}(R)\}$ term in Eq. (20-3) correspond to $\rho_{p-}$ and $\rho_{p+}$, respectively.

Where one seeks to satisfy the non-intersection condition in Eq. (12) for a consecutive sequence of slice indices, n=n1, n1+1, n1+2, . . . , n2 (n2>n1), one estimates a further intersection of permitted angles $$\rho_p(\text{total})=\rho_p(n=n1)\cap\rho_p(n=n1+1)\cap\rho_p(n=n1+2) \ldots \cap\rho_p(n=n2) \quad (23)$$

of the corresponding φ-constraint sets. The selected viewing angle β can be chosen within the ranges defined by Eq. (21-1) or (alternatively) Eq. (21-2).

Figure 10:
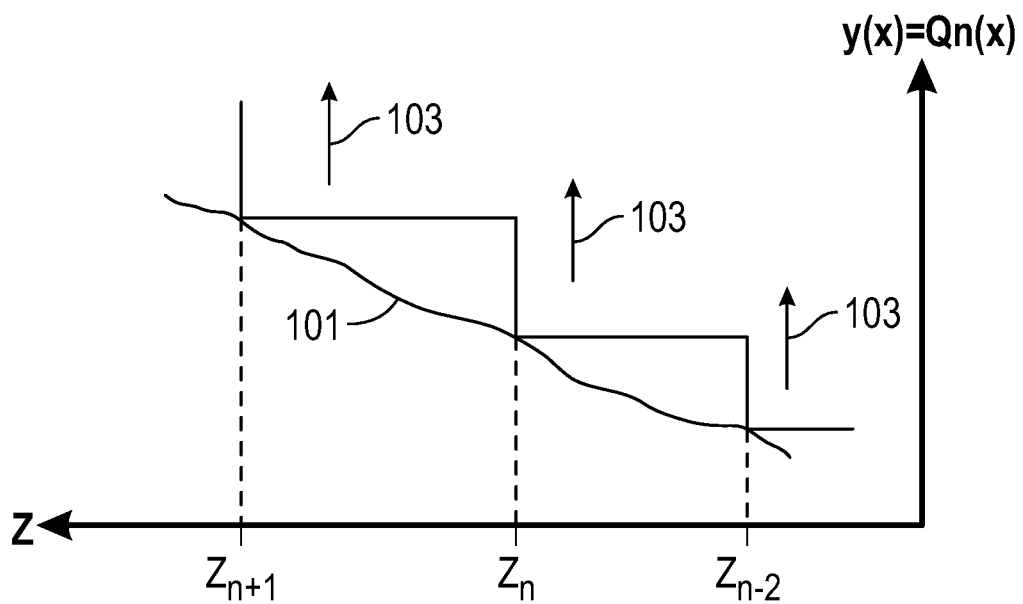
FIG. 10 shows the cross section of yz-plane and illustrates the construction of a femur or tibial jig relative to anatomical surface.
Figure 11:
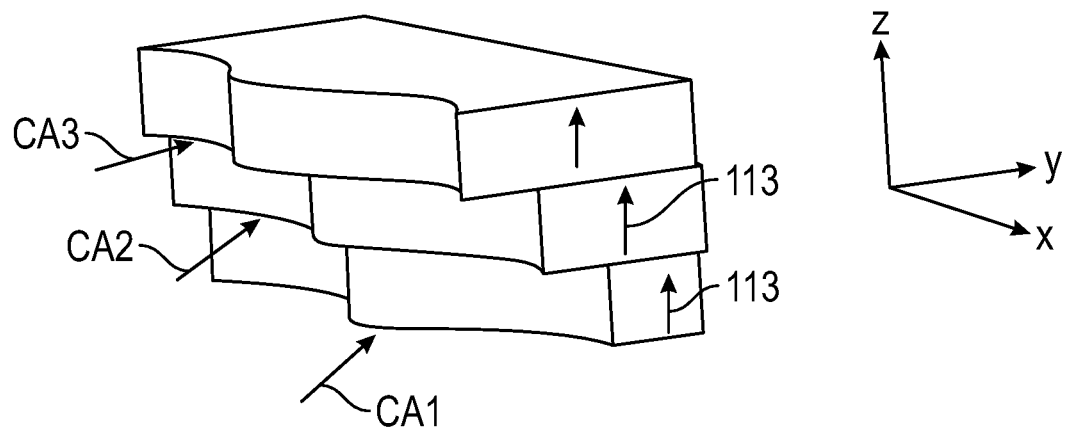
FIG. 11 shows the result of curve extrusion forming a STEP without any interference between the curves.
Figure 12:
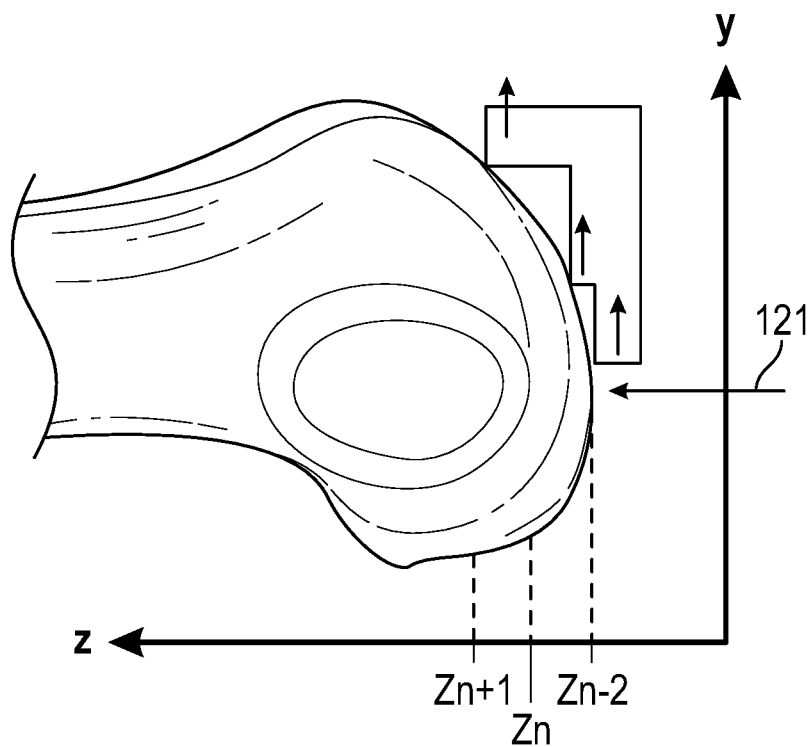
FIG. 12 shows a cross section sagittal view of the femur with the illustration of the same extrusion directions where three curvilinear segmented curves positioned above the distal point.
Figure 13:
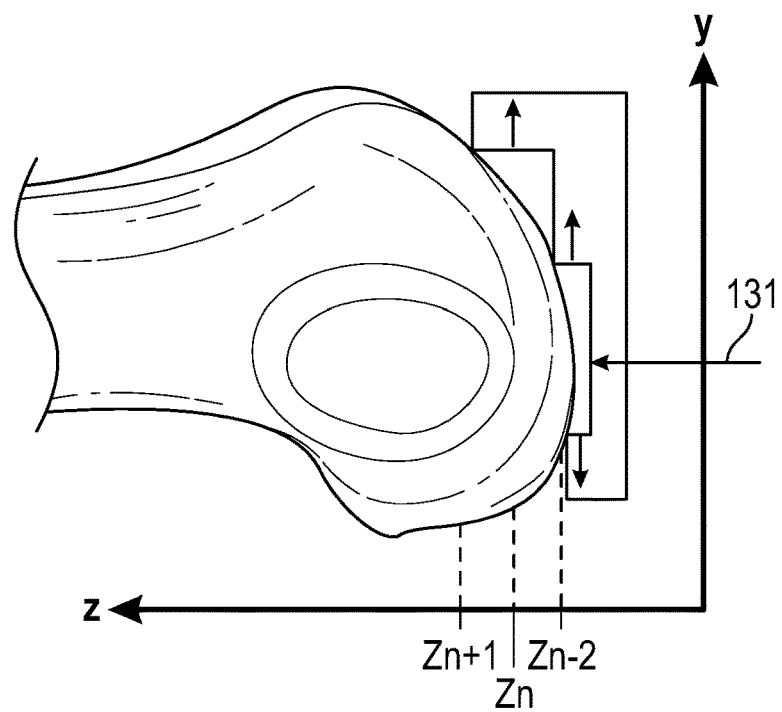
FIG. 13 shows a cross section sagittal view of the femur with the illustration of the extrusion directions where two curvilinear curves are positioned above the distal point and one curve below the distal point.

This condition is illustrated in FIG. 10 that shows the construction method on Y-Z plane. This condition leads to the selected curvilinear lines to be extruded in the direction 103 of φ(select) to assure that there is no interference between the extruded segmented curvilinear lines CA1, CA2, and CA3 and form a STEP structures as shown in FIG. 11 and the extrusion direction 113 is also determined against the surface of the anatomy (relative to the distal femur point 121) to assure that there is no interference between the jig and the surface of anatomy in FIG. 12. However, if one of the segmented lines is selected below the distal point 131, the extrusion direction is reversed to avoid any interference with anatomical surface as shown in FIG. 13.

Figure 14:
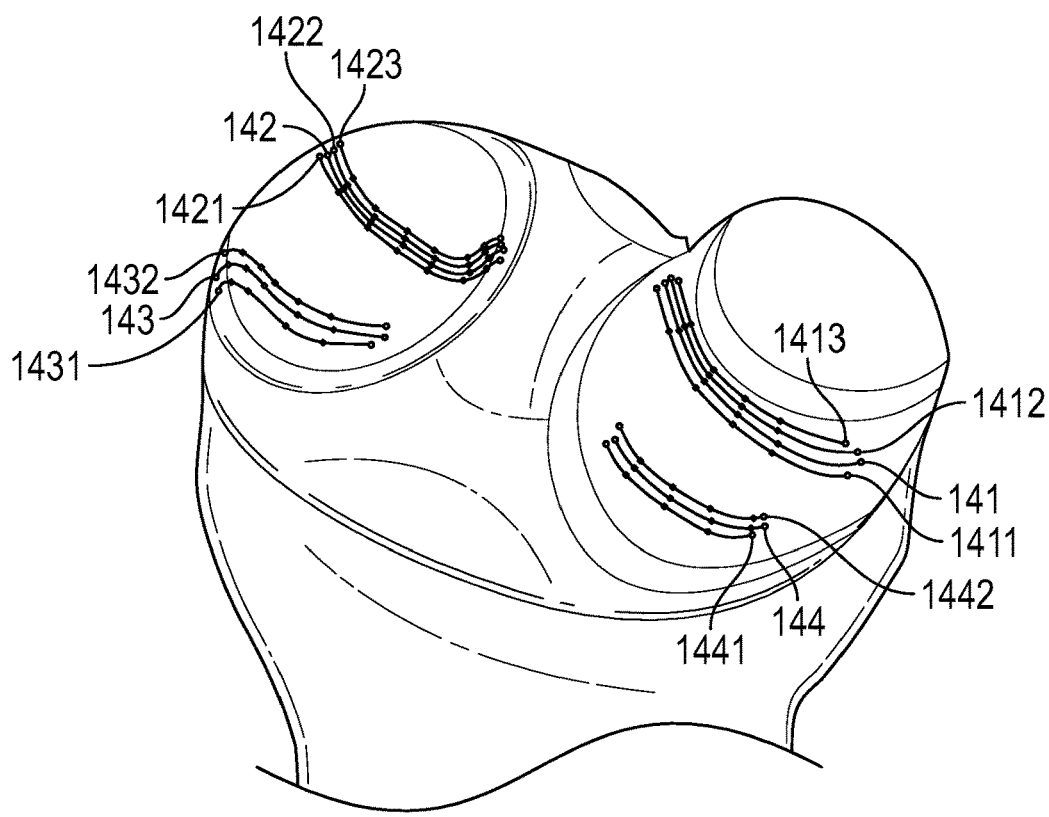
FIG. 14 illustrates the additional segmented lines in the neighborhood of the two selected curvilinear curves defined in FIGS. 6, 7, 8, and 9.
Figure 15:
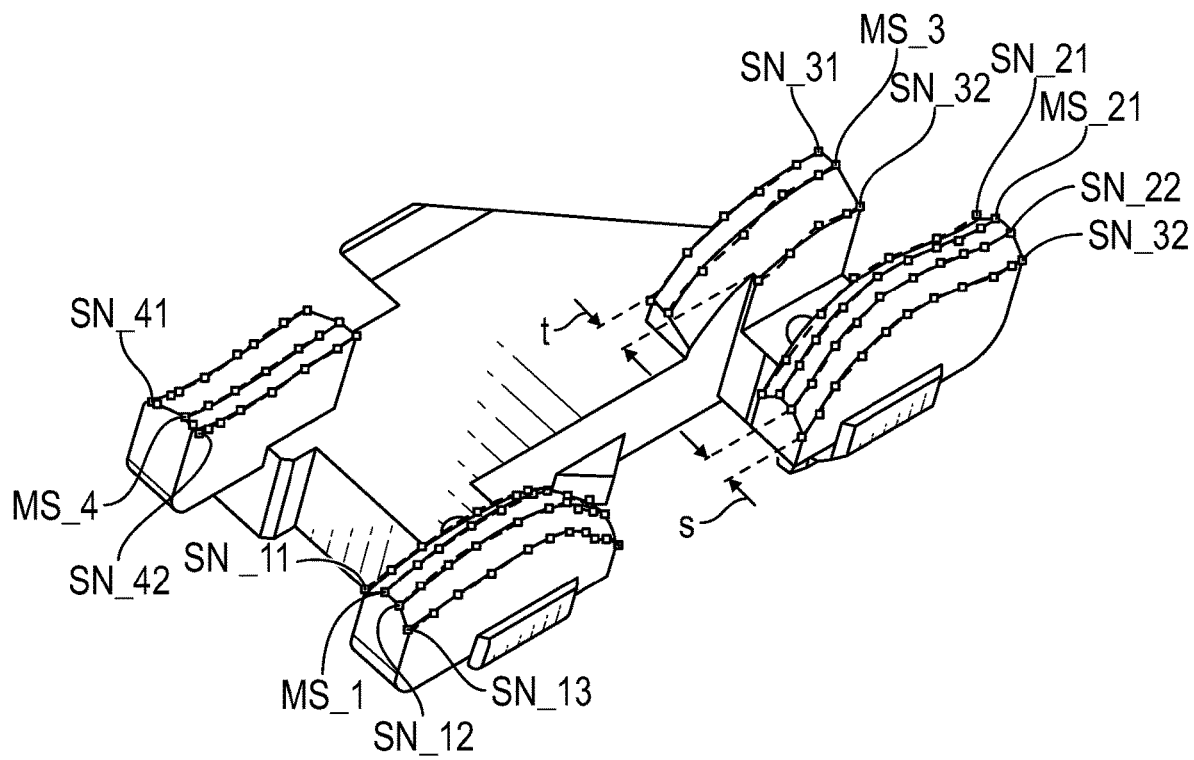
FIG. 15 shows the partial mating surfaces of the tibial jig constructed with additional segmented lines.
Figure 16:
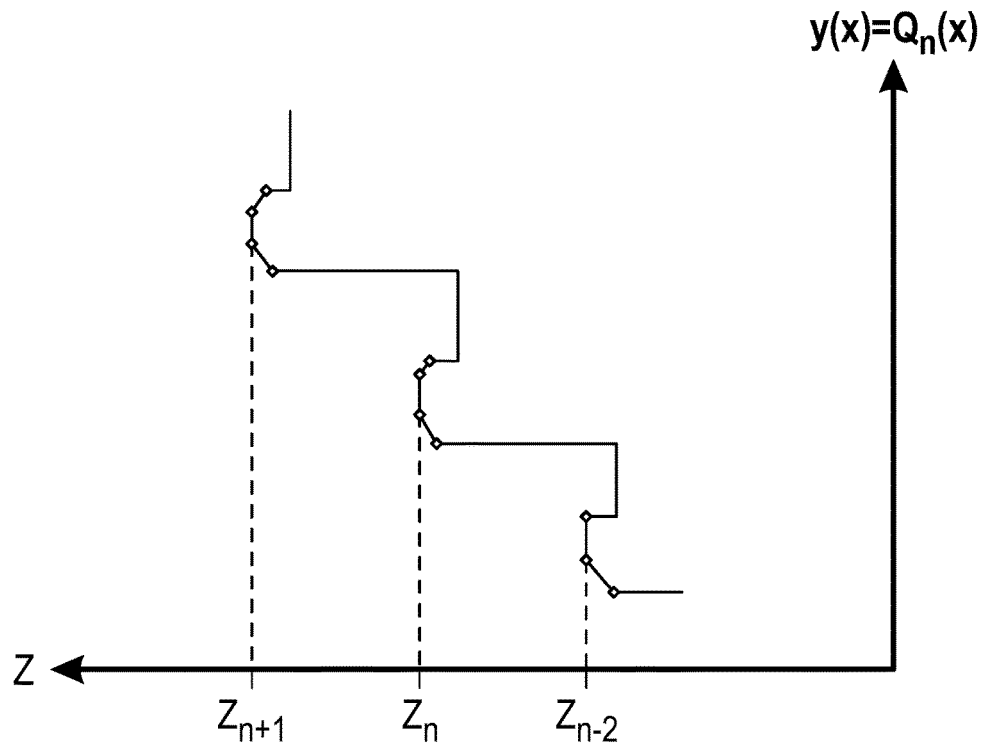
FIG. 16 illustrates the partial mating surfaces combined with a STEP feature in FIG. 11.

Although the selected segmented lines are optimal to mate the jig on the anatomical surface, there is uncertainty on the anatomical surface due to the random characteristics of joint arthritis. FIG. 14 exhibits that additional segmented lines are added in the neighborhood of each selected segmented line. In this example, four main segmented lines 141, 142, 143, 144 are seen, each of which are surrounded by two or three neighboring segmentations 1411, 1412, 1413, 1421, 1422, 1423, 1431, 1432, 1441, and 1442. The gap between the neighboring segmented lines is s=1 to 1.5 mm and the overall thickness is less than t=3 to 5 mm. Within the boundary of the thickness, 3-D surface is constructed as shown in FIG. 15. FIG. 16 shows that this method should be combined with the STEP structure illustrated in FIG. 11.

What is claimed is:

1. A method for defining contact curves of a cutting jig, comprising:
    obtaining a series of image slices of a patient's joint region;
    selecting a set of the image slices that show specified articular surface features in the joint region;
    characterizing patient-specific parameters from measurements obtained from the selected image slices so as to specify a set of curvilinear bone-jig contact surfaces and a cut plane, the patient-specific parameters being obtained from the selected image slices by: (1) obtaining a sequence of image slices, defining x-y image planes and a separation distance Δz between image slices: (2) forming at least one sequence of curves from projections of the image slices for one or more selected viewing angles φ relative to the respective x-y image planes, the curves following medial and lateral condyles of ends of respective femur and tibia proximate to a region of the knee as identified in the image slices, each curve approximated as a polynomial in its x y image plane then projected by geometric transformation onto rotated planes that correspond to the selected viewing angles φ; and (3) constraining viewing angles φ to meet a non-intersection condition on the respective sequences of curves; and
    manufacturing a jig in the form of a unitary piece combining a bone cutting guide and the set of curvilinear contact surfaces projecting from a jig substrate for abutting articular surface features, the curvilinear contact surfaces positioned according to the patient-specific parameters such that the curvilinear surfaces establish one and only one mechanical self-locking position for the unitary piece and the bone cutting guide defines the specified cut plane.

2. A method as in claim 1, wherein curvilinear contact surfaces are manufactured in accord with curves projected onto rotated planes for the constrained viewing angles by extruding step structures in the form of fins in the direction of the rotated planes and that terminate in a stepped set of line segments that follow the projected curves.

3. A method as in claim 1, wherein the manufactured jig is a femoral jig having a front plate coupled to an end plate at an elbow joint, the front plate having at least one planar slot therein coinciding with a desired cut plane when the jig is installed onto a femur, the front plate having a pair of anterior feet with curvilinear surfaces thereon for contact with anterior sides of respective medial and lateral condyles of the femur, the end plate having a pair of posterior feet with curvilinear surfaces thereon for contact with condylar surfaces of the respective medial and lateral condyles, the end plate also having a posterior projection proximate to the elbow joint and having a convex curvilinear surface for contact with trochlear groove surfaces in an intercondylar region of the femur.

4. A method as in claim 1, wherein the manufactured jig is a tibial jig having a main medial block and a front plate coupled to the main medial block at an elbow joint, the main plate having at least one planar slot therein coinciding with a desired cut plane when the jig is installed onto a tibia, an end extension projecting from a superior posterior surface of the front plate, the end extension having pairs of medial and lateral posterior feet with downward projections, the main medial block having a concave extension on an interior side of the elbow joint for contact with a side surface of the tibia, the downward projections of the posterior feet having underside curvilinear surfaces for contact with the medial and lateral condyles of the tibia at a position anterior to the tibial spine.

\* \* \* \* \*